(12) United States Patent
Kido et al.

(10) Patent No.: US 11,686,733 B2
(45) Date of Patent: Jun. 27, 2023

(54) METHOD FOR COLLECTING DATA TO PREDICT RISK OF DEVELOPING ALLERGIES

(71) Applicant: Applied Medical Enzyme Research Institute Corporation, Tokushima (JP)

(72) Inventors: Hiroshi Kido, Tokushima (JP); Makoto Irahara, Tokyo (JP); Koichi Suzuki, Tokushima (JP)

(73) Assignee: APPLIED MEDICAL ENZYME RESEARCH INSTITUTE CORPORATION, Tokushima (JP)

( * ) Notice: Subject to any disclaimer, the term of this patent is extended or adjusted under 35 U.S.C. 154(b) by 1199 days.

(21) Appl. No.: 16/098,492

(22) PCT Filed: May 11, 2017

(86) PCT No.: PCT/JP2017/017933
§ 371 (c)(1),
(2) Date: Feb. 14, 2019

(87) PCT Pub. No.: WO2017/195871
PCT Pub. Date: Nov. 16, 2017

(65) Prior Publication Data
US 2019/0391158 A1 Dec. 26, 2019

(30) Foreign Application Priority Data
May 13, 2016 (JP) .............................. JP2016-097337

(51) Int. Cl.
G01N 33/68 (2006.01)
G16B 40/00 (2019.01)

(52) U.S. Cl.
CPC ......... *G01N 33/6854* (2013.01); *G16B 40/00* (2019.02); *G01N 2800/24* (2013.01); *G01N 2800/50* (2013.01)

(58) Field of Classification Search
CPC ........... G01N 33/6854; G01N 2800/24; G01N 2800/50; G16B 40/00
See application file for complete search history.

(56) References Cited

U.S. PATENT DOCUMENTS

2004/0234614 A1 11/2004 Strong

FOREIGN PATENT DOCUMENTS

| JP | 1999142403 A | 5/1999 |
|---|---|---|
| JP | 2007524096 A | 8/2007 |
| JP | 2008107154 A | 5/2008 |
| JP | 2011-505557 A | 2/2011 |
| JP | 2011095132 A | 5/2011 |
| JP | 2012-511155 A | 5/2012 |
| WO | 2010110454 A1 | 9/2010 |

OTHER PUBLICATIONS

Eysink et al. 1999 (Relation between IgG antibodies to foods and IgE antibodies to milk, egg, cat, dog and/or mite in a cross-sectional study; Clinical and Experimental Allergy 29:604-610) (Year: 1999).*
Vidarsson et al. 2014 (IgG subclasses and allotypes: from structure to effector functions; Frontiers in Immunology; V5, Article 520, pp. 1-17) (Year: 2014).*
Caubet, Jean Christoph et al. "Significance of ovomucoid- and ovalbumin-specific IgE/IgG4 ratios in egg allergy" J Allergy Clin Immunol, vol. 129, No. 3, Mar. 2012, pp. 739-747.
Frechtel, Gustavo et al. "A case of allergy to human insulin associated with high IgG/IgE ratio for specific antibodies" J Invest Allergol Clin Immunol. Nov.-Dec. 1994; vol. 4(6): 320-323.
Kanemura, Norio et al. "Low-affinity allergen-specific igE in cord blood and affinity maturation after birth" J Allergy Clin Immunol , Mar. 2014, vol. 133, No. 3, 904-905.
Kawamoto, Norio et al. "Detection of ovomucoid-specific low-affinity IgE in infants and its relationship to eczema" Pediatr Allergy Immunol., Mar. 6, 2017, 28(4), 355-361.
Nakazato, Emiko "Relationship Specific IgE and IgG4 Antibody to Food Allergen and Other Allergic Factors in 0-Year Old Allergic Children—2 Sai Ijo Allergy Kanjigun tono Hikaku" Japanese Journal of Allergology, 1991, 40 (1), 8-20. [substitute for the English translation].
Sugimoto, Mayumi et al. "Differential response i n allergen-specific IgE, IgGs, and IgA levels for predictingoutcome of oral immunotherapy" Pediatr Allergy Immunol., Jan. 9, 2016, 27(3), 276-282.

* cited by examiner

*Primary Examiner* — Mary Maille Lyons
(74) *Attorney, Agent, or Firm* — Edwin S. Flores; Daniel J. Chalker; Chalker Flores, LLP

(57) ABSTRACT

A means for predicting an infant's risk of developing an allergy to an allergen is provided. IgG1 antibody titers and IgE antibody titers against egg white in a sample of infants 6 months old or younger are measured using a DCP chip, and a scattergram is created by plotting the IgG1 antibody titer on an X axis and the IgE antibody titer on a Y axis. For data distribution divided into two blocks, a linear function applicable to the respective blocks is calculated to obtain two types of linear functions, and the risk of developing an allergy is predicted based on which block an infant belongs to.

3 Claims, 9 Drawing Sheets

[Figure 1]
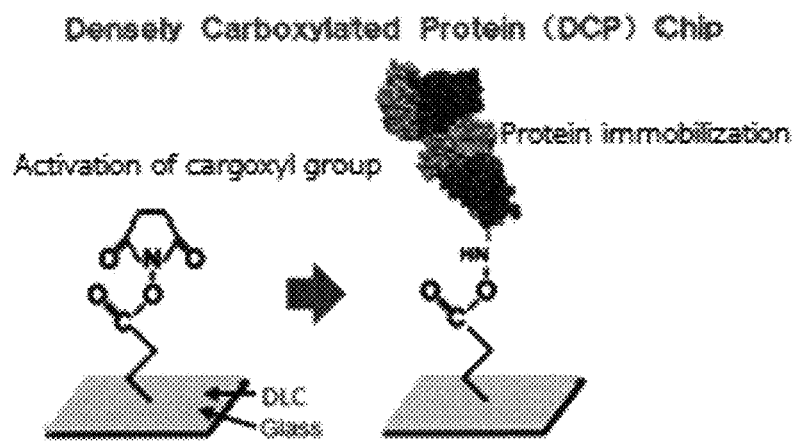

[Figure 2]
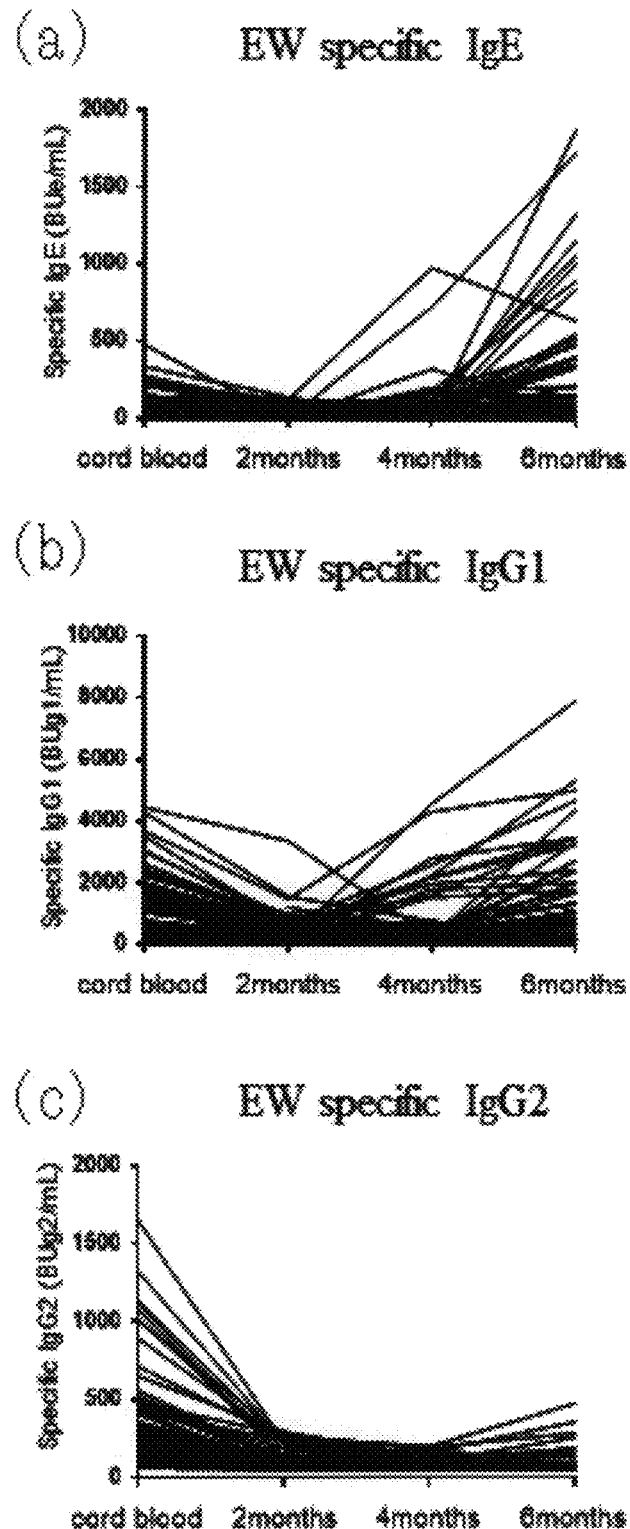

[Figure 3]
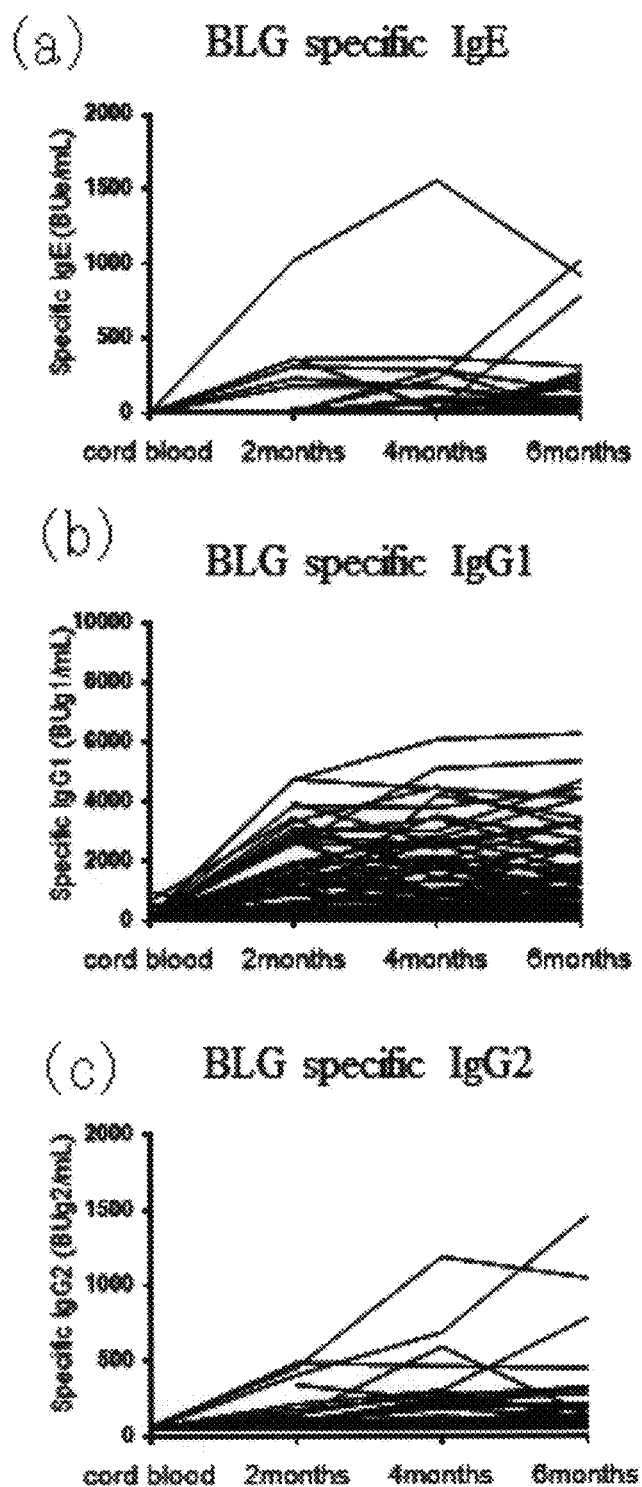

[Figure 4]
(a)
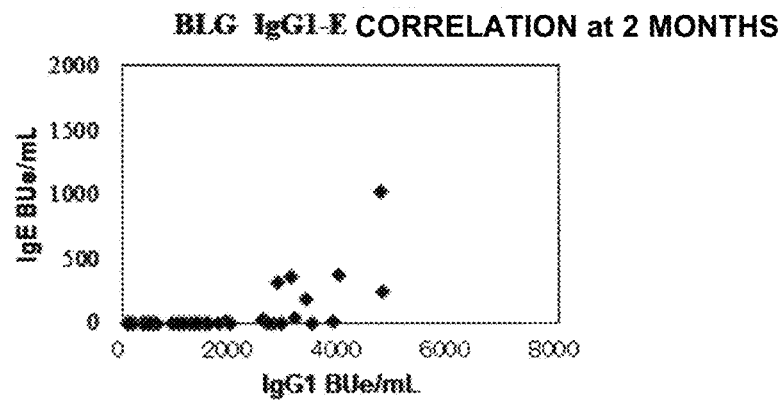
(b)
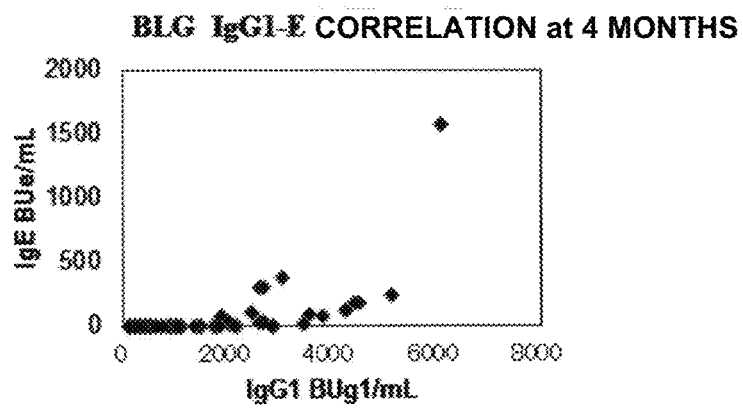
(c)
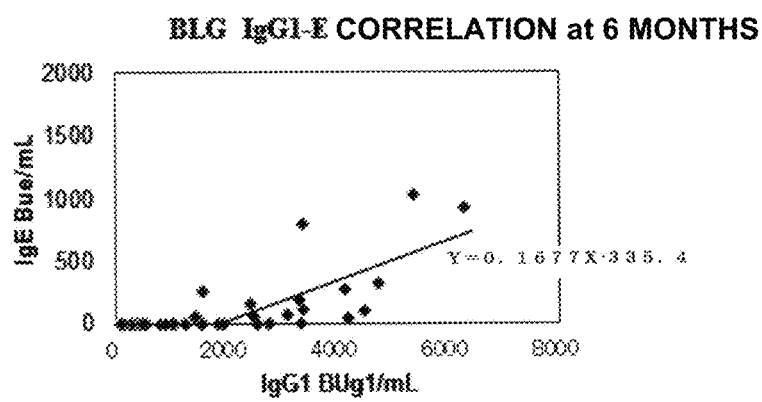

[Figure 5]
(a)
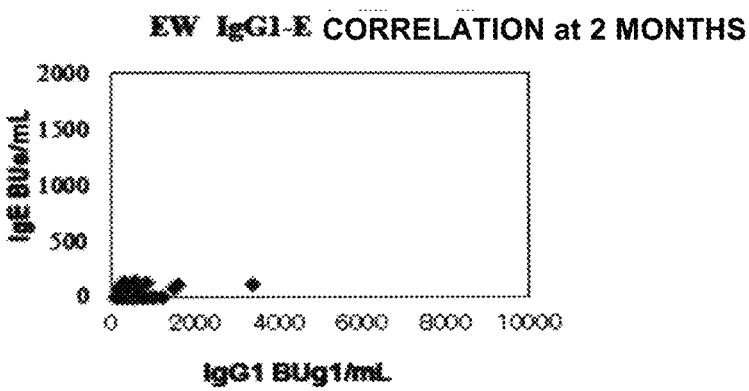
(b)
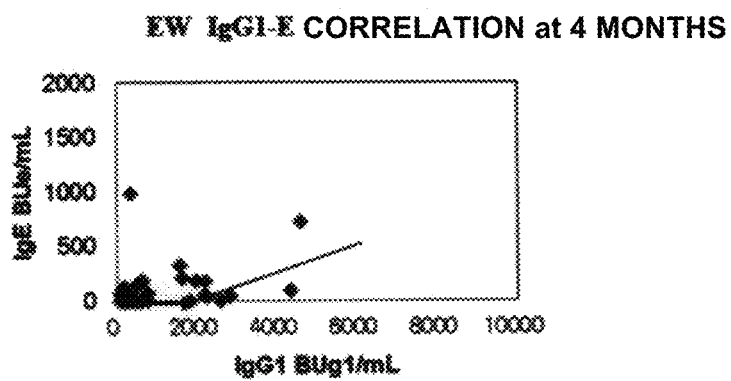
(c)
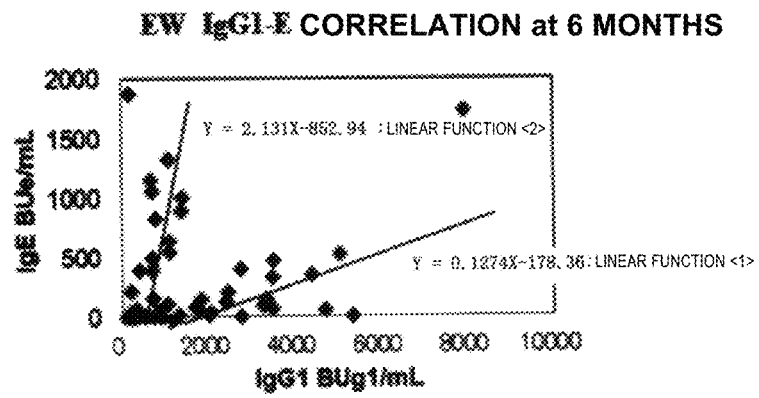

[Figure 6]
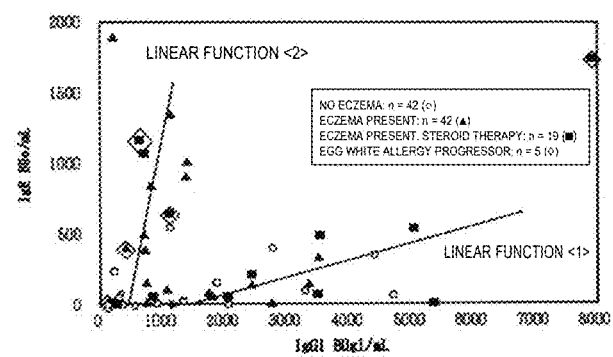

[Figure 7]
(a)
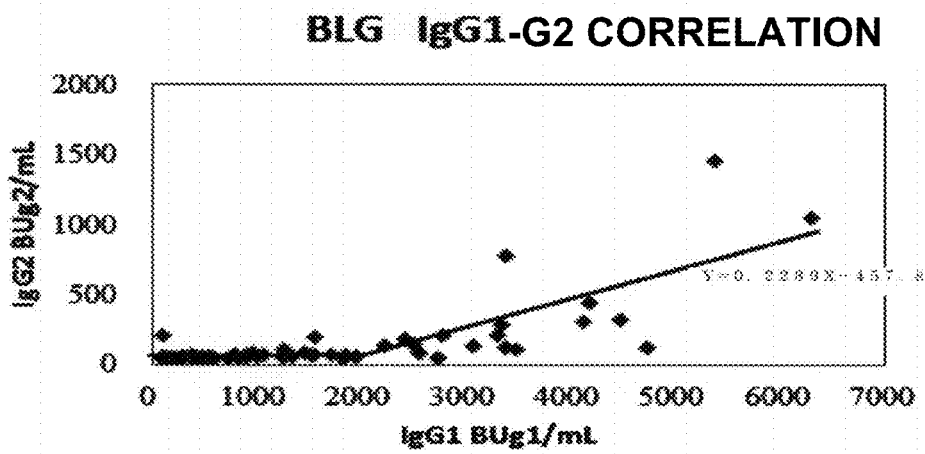
(b)
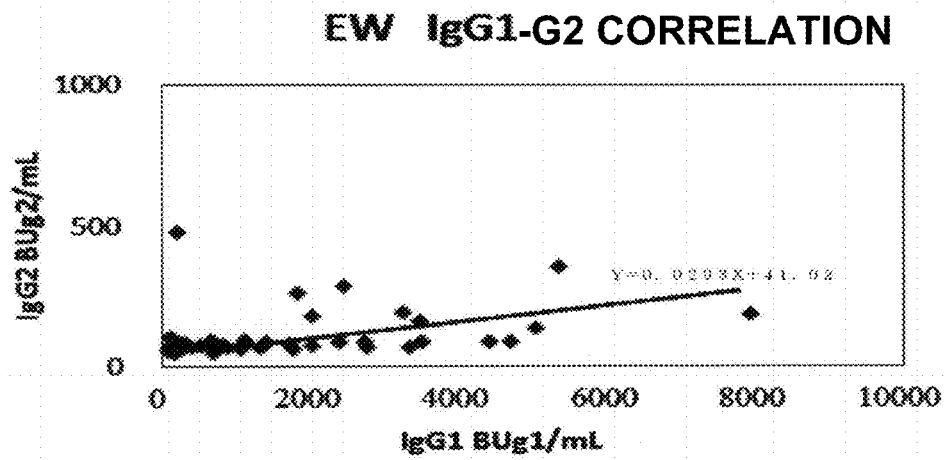

[Figure 8]
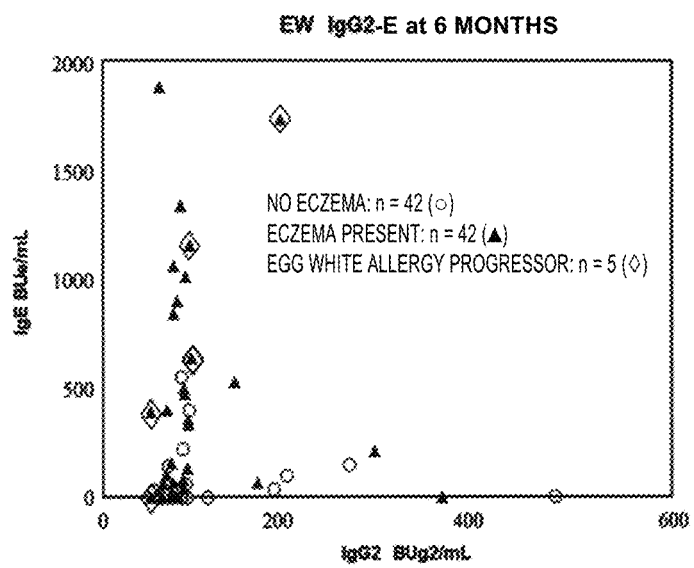
[Figure 9]
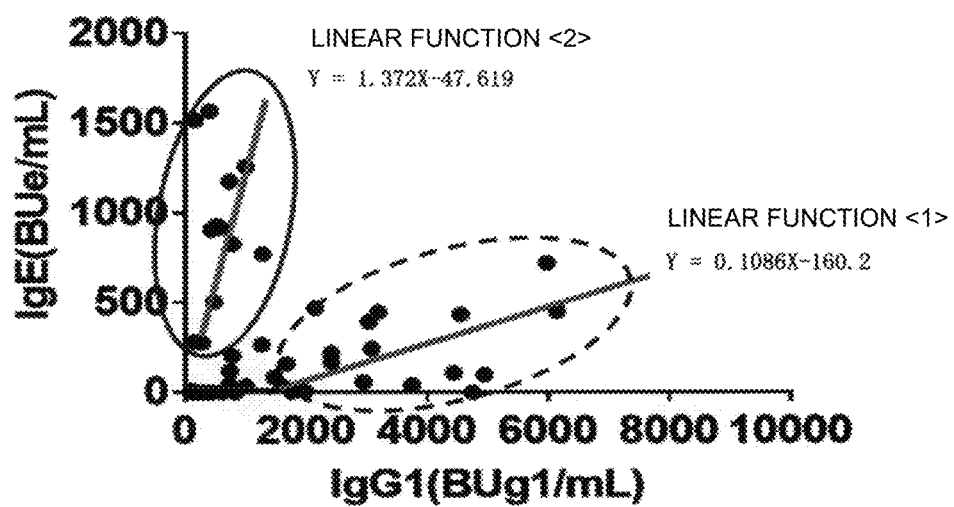

[Figure 10]
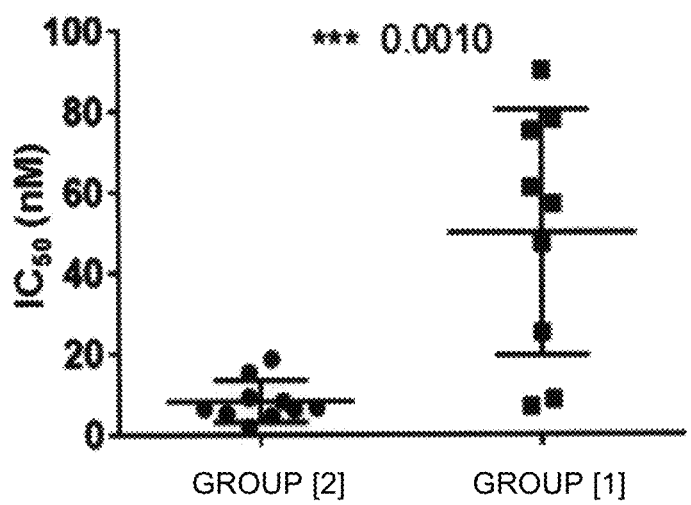

METHOD FOR COLLECTING DATA TO PREDICT RISK OF DEVELOPING ALLERGIES

CROSS-REFERENCE TO RELATED APPLICATIONS

This application is the National Stage of International Application No. PCT/JP2017/017933, filed on May 11, 2017 claiming the priority of JP 2016-097337, filed on May 13, 2016, the content of each of which is incorporated by reference herein.

TECHNICAL FIELD

The present invention relates to a method for collecting data to predict an infant's risk of developing an allergy to an allergen, the method comprising: quantitatively measuring each of IgG1 and IgE antibody titers against an allergen in a sample collected from the infant; and referring to an evaluation criterion established based on a level of immunoglobulin class switching from IgG1 to IgE, which has been previously statistically processed.

BACKGROUND ART

An allergy is a reaction harmful to living bodies, which is caused by entry of a causative substance into the body. Humans maintain life by digesting and absorbing different species as food, and thus undigested foreign substances left unabsorbed are always incorporated into the body. Oral immune tolerance (immunotolerance) normally functions to prevent a protective response (allergic reaction) of living bodies to the undigested and absorbed foreign substances from occurring. However, 5 to 10% of newborn infants are considered to develop some food allergy by 1 year old. The pathogenesis of allergy and methods for prediction thereof have not been completely elucidated.

Widely known allergies include pollinosis, atopic dermatitis and food allergies which are considered to be associated with IgE antibody. However, some findings explain involvement of not only IgE dependent reaction but also IgE independent reaction in which the blood IgE level is inconsistent with allergic symptoms; and other findings describe that antigen specific antibodies induced by entry of an allergen into the body include IgA and IgG isotypes in addition to IgE, and the total effects of these antibodies cause allergic symptoms. Treatments such as a process of subjecting to an immunotolerance vaccination program including one or more antigen and oral desensitization therapy in which antigen is ingested are known. In diagnosis, a process of measuring the level of IgA, various IgG and IgE antibodies specific to antigen in a biological sample of individuals, an intracutaneous test for antigen, and a scratch test (prick test) in which a small scratch is made on the skin to allow antigen to enter are performed, and with an overall assessment of the results, the condition of progress of allergy is investigated and treatment is evaluated. However, definite diagnostic methods have not yet been established. So far a method of assessing therapeutic potential of the above vaccination program has been reported (see, for example, patent document 1); and it has also been reported that reactivity of an allergen specific immunoglobulin generated in the saliva by adding dietary allergen and causing an antigen-antibody reaction with an antibody in the saliva is measured, and the results are compared with the measured value of IgE and IgG isotypes of healthy individuals, and immunoassay can be performed based on the correlation (see, for example, patent document 2). In recent years, as details of production of various types of antigen specific immunoglobulin have been analyzed based on immunoglobulin class switching recombination (see, for example, non-patent documents 1 and 2), there is a pressing need for assessing allergenic conditions in relation to measured values of various immunoglobulins.

PRIOR ART DOCUMENTS

Patent Documents

Patent Document 1: Japanese unexamined Patent Application Publication (Translation of PCT Application) No. 2007-524096
Patent Document 2: Japanese unexamined Patent Application Publication No. 11-142403

Non-Patent Documents

Non-patent Document 1: Xiong H, Dolpady J, Wabl M, Curotto de Lafaille M A, Lafaille J J. Sequential class switching is required for the generation of high affinity IgE antibodies. J Exp Med 2012; 209:353-64.
Non-patent Document 2: Collins A M, Jackson K J. A Temporal model of human IgE and IgG antibody function. Front Immunol 2013; 4: 235.

SUMMARY OF THE INVENTION

Object to be Solved by the Invention

An object of the present invention is to provide a means for predicting an infant's risk of developing an allergy.

Means to Solve the Object

The present inventors have measured IgG1 antibody titers and IgE antibody titers against egg white (EW) in a blood plasma sample of 6-month or younger infants using a DCP (Densely carboxylated protein) chip and created a scattergram by plotting the IgG1 antibody titers on an X axis and the IgE antibody titers on a Y axis, and as a result have found that the distributed data is divided into two blocks. Linear functions applicable to the respective blocks were calculated and as a result two types of linear functions were obtained: linear function [1] that rises at IgG1=1,400 BUg1 and linear function [2] that rises before IgG1=1,400 BUg1 is reached. It has been found that infants who were diagnosed as having acquired immune tolerance without abnormal symptoms even after ingestion of EW (hereinafter also referred to as infants with established immune tolerance) in diagnosis of an allergy at 1 year old belong to the block to which the above linear function [1] is applied, while many of the infants who were diagnosed as EW allergy have history of eczema lasting more than one week during the development until 6 months old and belong to the block to which the above linear function [2] is applied.

Thus, we have confirmed that the risk of developing an allergy to an allergen can be predicted by measuring IgG1 antibody titers and IgE antibody titers in a sample of an infant and referring to a level of immunoglobulin class switching (hereinafter also simply referred to as "class switching") from IgG1 to IgE, which has been previously statistically processed. Furthermore, since the infants with established immune tolerance showed a pattern of IgG2 increase, while most of the infants with a diagnosis of EW allergy showed a low value of both IgG1 and IgG2, a difference was found in class switching from IgG1 to IgG2 between the infants with established immune tolerance and the infants who developed an allergy.

Furthermore, the present inventors have found that in those who belong to the block to which linear function [2] is applied and developed eczema and received treatment of steroid application to the skin up to 6 months old, the incidence of EW allergy at diagnosis of food allergy at 1 year old was lower than that in infants without steroid application, and thus have completed the present invention.

Effect of the Invention

The present invention enables collection of data for predicting an infant's risk of developing an allergy to an allergen in infancy by quantitatively measuring each of IgG1 and IgE antibody titers against an allergen in a sample collected from the infant.

Accordingly, the present invention is as follows.

[1] A method for collecting data to predict an infant's risk of developing an allergy to an allergen in infancy, the method comprising: quantitatively measuring each of IgG1 and IgE antibody titers against the allergen in a sample collected from the infant; and referring to an evaluation criterion established based on a level of immunoglobulin class switching from IgG1 to IgE, which has been previously statistically processed.

[2] The method according to [1] above, wherein the IgG1 and IgE antibody titers against the allergen in the sample are quantitatively measured by using a DCP chip.

[3] The method according to [1] or [2] above, wherein the sample is blood plasma or blood serum.

[4] The method according to any one of [1] to [3] above, wherein the statistical processing comprises creating a scattergram by plotting the IgE antibody titer and the IgG1 antibody titer and obtaining a linear function by regression analysis.

[5] The method according to any one of [1] to [4] above, wherein the risk of developing an allergy to the allergen is predicted by a method comprising the following steps (a) to (d):

(a) quantitatively measuring each of IgG1 and IgE antibody titers against the allergen in the sample collected from the infant;

(b) creating a scattergram by plotting the IgG1 antibody titer on an X axis and the IgE antibody titer on a Y axis;

(c) calculating a correlation between the IgG1 antibody titer and the IgE antibody titer by regression analysis into: (1) linear function 1 ($Y1=aX1-b$ wherein $a>0$, $b>0$) applied to data of an infant having a low risk of developing an allergy to the allergen; and/or (2) linear function 2 ($Y2=cX2-d$ wherein $c>a$) applied to data of an infant having a high risk of developing an allergy to the allergen; and (d) predicting that an infant belonging to a block to which linear function 1 is applied has a low risk of developing an allergy to the allergen and an infant belonging to a block to which linear function 2 is applied has a high risk of developing an allergy to the allergen.

[6] The method according to any one of [1] to [5] above, wherein the evaluation criterion further comprises an IgG2 antibody titer in the sample collected from the infant.

[7] The method according to [6] above, wherein the IgG2 antibody titer in the sample collected from the infant is included in the evaluation criterion by a method comprising the following steps (e) to (h):

(e) quantitatively measuring each of IgG1 and IgG2 antibody titers against the allergen in the sample collected from the infant;

(f) creating a scattergram by plotting the IgG1 antibody titer on an X axis and the IgG2 antibody titer on a Y axis;

(g) calculating a correlation between the IgG1 antibody titer and the IgG2 antibody titer by regression analysis into linear function 3 ($Y3=eX3-f$ wherein $e>0$) applied to data of an infant having a low risk of developing an allergy to the allergen; and (h) predicting that an infant who shows an IgG1 value smaller than an X-axis intercept (IgG1 antibody titer=$f$/eBug1/mL) of a linear function has a high risk of developing an allergy to the allergen.

[8] The method according to any one of [1] to [7] above, wherein the evaluation criterion further comprises a level of affinity of IgE antibody for the allergen in the sample collected from the infant.

BRIEF DESCRIPTION OF THE DRAWINGS

FIG. 1 A schematic view of a DCP chip on which protein has been immobilized.

FIG. 2 A graph obtained by measuring antibody titers of (a) IgE antibody, (b) IgG1 antibody and (c) IgG2 antibody against EW in a cord blood sample of each infant; and samples collected from 84 infants aged 2 months, 4 months and 6 months.

FIG. 3 A graph obtained by measuring antibody titers of (a) IgE antibody, (b) IgG1 antibody and (c) IgG2 antibody against β-lactoglobulin (BLG) in a cord blood sample of each infant; and samples collected from 84 infants aged 2 months, 4 months and 6 months.

FIG. 4 A graph plotting correlation between IgG1 antibody titers and IgE antibody titers against BLG in a sample collected from 84 infants aged 2 months (a), 4 months (b) and 6 months (c).

FIG. 5 A graph plotting correlation between IgG1 antibody titers and IgE antibody titers against EW in a sample collected from 84 infants aged 2 months (a), 4 months (b) and 6 months (c).

FIG. 6 A graph plotting correlation between IgG1 antibody titers and IgE antibody titers against EW in a sample collected from 84 infants aged 6 months, which also includes information on the presence of eczema and whether or not steroid has been applied to the site with eczema until the 6-month checkup, and diagnosis of the development of EW allergy at 1 year old.

FIG. 7 A graph plotting correlation between IgG1 antibody titers and IgG2 antibody titers against BLG (a) and EW (b) in a sample collected from 84 infants aged 6 months.

FIG. 8 A graph plotting IgG2 antibody titers and IgE antibody titers against EW in a sample collected from 84 infants aged 6 months.

FIG. 9 A graph plotting IgG1 antibody titers and IgE antibody titers against ovalbumin (OVA) in a sample collected from 78 breast-fed/mixed-fed infants aged 6 months.

FIG. 10 A graph plotting the concentrations of an allergen inhibiting 50% of binding of OVA, $IC_{50}$ values (nM) in Group 1 and Group 2.

MODE OF CARRYING OUT THE INVENTION

The method for collecting data of the present invention is not particularly limited as long as the method is for collecting data to predict an infant's risk of developing an allergy to an allergen by quantitatively measuring each of IgG1 and IgE antibody titers against an allergen in a sample collected from the infant and referring to an evaluation criterion established based on a level of class switching from IgG1 to IgE, which has been previously statistically processed. The infant according to the present invention is not particularly limited to those "from birth to under 1 year of age" as provided in the Child Welfare Act in that the benefit of the method for predicting a risk of developing an allergy of the present invention can be received. The method may include, for example, a method in which a sample is collected from an infant aged, for example, 4 to 8 months, preferably 5 to 7 months (hereinafter referred to as "6 months" by taking their average), when immunoglobulin class switching from, in particular, IgG1, is said to be explicit, and data is collected for predicting whether the infant's risk of developing an allergy to an allergen is high or low in infancy when the infant is 8 to 16 months old, preferably 10 to 14 months old, and more preferably 11 to 13 months old. Furthermore, data for comprehensive prediction can be collected in consideration of individual differences by quantitatively measuring IgE antibody titers, IgG1 antibody titers and if necessary IgG2 antibody titers against the above allergen over time during a period from 0 to 12 months of age. Class switching refers to occurrence of change in the constant region (Fc region) without change in the variable region by gene rearrangement at a gene locus of various antigen specific antibodies in a biological reaction against foreign substances entering into the body. In addition to a route of transformation of IgM→IgG3→IgG1→IgG2→IgG4, a route of IgM→IgG3→IgG1→IgE is known.

Examples of allergens in the present invention, which are not particularly limited as long as the allergen is an antigen protein or peptide that is capable of inducing production of antibody in a human, include peptides which are food allergens, such as eggs, milk, meat such as beef, fish such as salmon and tuna, crustaceans such as shrimp and crab, mollusks, cereals, beans and nuts, fruits, vegetables, brewer's yeast and gelatin. More specifically, examples thereof include milk allergens such as αs1-casein, αs2-casein, β-casein, κ-casein, α-lactalbumin and β-lactoglobulin (BLG) which is the main component of whey allergen, egg white (EW) allergens such as ovomucoid, ovalbumin (OVA), conalbumin or a mixture thereof, egg allergens such as egg yolk allergen, wheat allergens such as gliadin and gluten, buckwheat allergen, peanut allergens such as Ara h1, sesame allergens such as lis globulin and crustacean allergens such as tropomyosin protein. A single allergen having a known molecular weight is preferable as an allergen used for calculating affinity of an antibody for the allergen as an $IC_{50}$ value (the concentration of an allergen inhibiting 50% of binding), considering that antigen concentration (nM) is used as an index.

The above allergen peptides may include chemically modified peptides such as glycosylated peptide, phosphorylated peptide, acylated peptide, acetylated peptide, methylated peptide and ubiquitinated peptide. The chemically modified peptide may be chemically modified natural peptide and chemically modified artificial peptide. Furthermore, it is preferable to use, as a peptide containing an allergen epitope, an epitope-containing peptide in which at least two amino acids are added to the N-terminal and/or C-terminal of a 7 to 15 amino acid long peptide portion binding to a MHC class II molecule, because the peptide reacts with an antibody in a patient at a sensitivity of several to several ten times. The peptide containing an allergen epitope such as the epitope-containing peptide in which at least two amino acids are added to the N-terminal and/or C-terminal of a peptide portion binding to a MHC class II molecule may be prepared by peptide synthesis, or may be prepared as a protease-decomposed peptide. Examples of proteases include trypsin, chymotrypsin, cathepsin and lysyl endopeptidase.

The sample in the present invention is not particularly limited as long as the sample is collected from an infant and enables quantitative measurement of each of IgG and IgE antibody titers against the above allergen. Examples thereof include body fluid collected from an infant, such as blood, blood serum, blood plasma, saliva, tear fluid, nasal discharge and urine, and blood and blood plasma are preferred. In the case of using blood serum as a sample, for example, blood is collected from the brachial vein of an infant, and the blood collected is left to stand at 4° C. overnight and then centrifuged, and the supernatant can be used as blood serum. Alternatively, as small as 50 to 100 μL of blood obtained by minimally puncturing the ear lobe or fingertip with a needle for collecting very small amounts of blood is collected by a microcapillary tube, and may be directly used.

Examples of allergies which are the subject of a risk of development in the present invention include pathological conditions caused by, for example, oral sensitization or percutaneous sensitization to a specific allergen, leading to symptoms of: skin symptoms (itching, urticaria, angioedema, redness, eczema), mucous membrane symptoms (eye symptoms: conjunctival hyperemia, edema, itching, lacrimation, eyelid edema), nasal symptoms (sneezing, nasal discharge, nasal congestion), oropharyngeal symptoms (discomfort and swelling in the oral cavity, lips and tongue, itchy and irritating throat), gastrointestinal symptoms (stomach ache, nausea, vomiting, diarrhea, bloody stools), respiratory symptoms (throat constriction, pharyngeal edema, hoarseness, cough, wheezing, dyspnea, asthma) and systemic symptoms (anaphylactic shock, tachycardia, collapse, disturbed consciousness, decreased blood pressure).

The evaluation criteria for predicting a risk of developing an allergy to an allergen are not particularly limited as long as the criteria are prepared based on a level of class switching from IgG1 to IgE, which has been previously statistically processed. The level of class switching from IgG1 to IgE in the present invention may include a level of class switching to IgE occurring after sufficient accumulation of IgG1 and a level of class switching to IgE occurring before sufficient accumulation of IgG1. The evaluation criteria may also include a level of class switching from IgG1 to IgG2, and a level of class switching from IgG1 to IgG2 may include a level of class switching to IgG2 occurring after sufficient accumulation of IgG1, and the case in which sufficient accumulation of IgG1 and an increase in IgG2 cannot be seen.

In an infant, class switching to IgE after sufficient accumulation of IgG1 may occur when oral immune tolerance has been established. The risk of developing an allergy to an allergen can be predicted to be low in such cases. Class switching from IgG1 to IgG2 may also occur simultaneously when oral immune tolerance has been established. The risk of developing an allergy to an allergen can be predicted to be low in such cases.

The above oral immune tolerance may include a phenomenon in which after the antibody level of IgG1 produced in the infant reaches a threshold, the IgE antibody titer is increased and then is decreased, in a foreign-body reaction in an infant to an undecomposed substance entering into the body of the infant by ingestion, through breast milk, of the undecomposed substance which his/her mother has eaten, or by ingestion of formula milk. A phenomenon in which after the antibody level of IgG1 produced in an infant reaches a threshold, the IgG2 antibody titer is slowly increased may also be included.

The above class switching to IgE before sufficient accumulation of IgG1 produced in an infant himself may occur when percutaneous sensitization through the skin takes place. In this case, symptoms of eczema may be frequently found in the infant. The risk of developing an allergy to an allergen in such an infant can be predicted to be high.

The above percutaneous sensitization means a phenomenon in which extensive class switching from IgG1 to IgE occurs before the antibody level of IgG1 reaches a threshold with a deviation from the mechanism of oral immune tolerance. The deviation from the mechanism of oral immune tolerance means that attachment of an undecomposed component of an allergen eaten by a mother to the skin of an infant or direct attachment of an allergen in environment to the skin of an infant triggers eczema or a reduced barrier function of the skin of an infant, allowing the allergen to enter into the body of the infant.

Examples of methods of statistical processing of a level of class switching from IgG1 to IgE include a method in which a scattergram is created by plotting IgG1 antibody titers on an X axis and IgE antibody titers on a Y axis in a sample collected from an infant and calculating a correlation between the IgG1 antibody titer and the IgE antibody titer by regression analysis into a linear function. The above statistical processing is advantageous in that the timing of class switching and the threshold of IgG1 can be predicted for the whole set of data in the region (block) to which the function can be applied even if the data includes individual differences and differences in allergens.

The linear function obtained by the above statistical processing includes: (1) linear function 1 ($Y1=aX1-b$ wherein $a>0$, $b>0$) applied to data of an infant having a low risk of developing an allergy to an allergen; and (2) linear function 2 ($Y2=cX2-d$ wherein $c>a$) applied to data of an infant having a high risk of developing an allergy to an allergen.

Linear function 1 described above can be applied to all data in a scattergram when the data contains data of infants with a low risk of developing an allergy to an allergen, and linear function 2 described above can be applied to all data in a scattergram when the data contains only data of infants with a high risk of developing an allergy to an allergen. When it is difficult to apply either one of the above linear functions to all data in a scattergram, the data is divided into two blocks, and linear function 1 which is applied to the data of infants with a low risk of developing an allergy to an allergen and linear function 2 which is applied to the data of infants with a high risk of developing an allergy to an allergen can be obtained for each block. Examples of methods of dividing data into two blocks when it is difficult to apply a linear function to all data in a scattergram include suitable statistical measures such as constructing a program so that the correlation coefficient is high; and dividing into 2 blocks according to assessment of those skilled in the art, e.g., a data collector and a data analyst, based on the actual state of distribution of data.

The threshold of IgG1 may be obtained as the antibody titer of $IgG1=b/a$ BUg1/mL at the position of the rise of the above linear function 1 in the graph. In the above linear function 2, the antibody titer of IgG1 (d/c) (wherein preferably $d>0$) at the position of the rise of the graph is smaller than $b/a$ BUg1/mL. It can be predicted that an infant having an IgG1 value exceeding the threshold has a lower risk of developing an allergy even with a high IgE antibody titer.

The data for predicting a risk of developing an allergy according the present invention may include IgG2 antibody titers in a sample of a 6-month old infant, for example, at 6-month checkup. Since the class switching to IgE occurs before the IgG1 antibody titer reaches the threshold, the risk of developing an allergy can be predicted to be high when the IgG2 antibody titer is kept low. Furthermore, history of development of rush which has lasted for more than one week, which has been found in 6-month checkup, may also be included in the evaluation criteria for predicting a higher risk of developing an allergy.

In the present invention, subject infants whose risk of developing an allergy to an allergen is predicted can be included as the infant in the method of collecting data of the present invention by inputting the data of the subject infants themselves. This improves accuracy of the evaluation criteria in the present invention.

The risk of developing an allergy can be reduced by using the method for collecting data to predict a risk of developing an allergy of the present invention. Examples of methods of such reduction includes a method in which development of an allergy is prevented by transdermal administration (application) of steroid to sites where rash is present in an infant who has been predicted to has a high risk of developing an allergy and a method of increasing oral immune tolerance. Examples of methods of the above transdermal administration of steroid include a method in which steroid of various potency ranks is applied to sites with rash once or twice a day depending on the severity as described in the Guidelines for the Treatment of Atopic Dermatitis 2016 (Guidelines of the Japanese Dermatological Association) (The Japanese Journal of Dermatology 126(2):121-155, 2016). Examples of methods of increasing oral immune tolerance described above include methods of continuous and safe ingestion of a very small amount of antigen with reduced antigenicity, which is contained in breast milk.

In the present invention, methods of quantitatively measuring each of the antibody titers of IgG1 and IgE, and IgG2 are not particularly limited as long as the method is capable of quantifying the concentration of IgG1, IgE and IgG2 antibodies binding to an allergen in a sample collected from an infant in terms of an antibody titer (Binding Unit:BU)/mL. Preferred examples thereof include a method using a chip which can immobilize antigens and can quantitatively measure the antigen-antibody reaction when an antibody for the specific antigen which has been immobilized is present. Specific examples thereof include methods of quantitative measurement described in Kamemura N, et al. J Allergy Clin Immunol 2012; 130:113-121 and Suzuki K. et al. Anal Chim Acta 2011; 706:321-327.

The data for predicting a risk of developing an allergy according the present invention may include a level of affinity of IgE antibody for an allergen in a sample of a 6-month old infant. More specifically, when the affinity of IgE antibody for an antigen (an allergen) is measured in a sample of an infant containing IgE antibody at such a level that the affinity of IgE antibody can be measured, the risk of developing an allergy can be predicted to be higher if the affinity of IgE for allergen is high; and the risk of developing an allergy can be predicted to be lower if the affinity of IgE for allergen is low. The level of IgE antibody at which the affinity of IgE antibody can be measured needs to be at least the confidence limit of the measurement. The confidence limit of the measurement varies depending on types of allergens, and for example, is 100 BUe/mL or more for the affinity of IgE for OVA.

Examples of methods of measuring the affinity of IgE antibody for a specific allergen include a method of measuring affinity of antibody by a known assay system such as FACS, BIACORE, RIA and ELISA. Preferred examples include ELISA competitive inhibition assay in which binding activity of antibody to an allergen is quantitatively compared and analyzed using competitive inhibition in an antigen-antibody reaction. In a specific procedure, an allergen is added as a competitive substance to a sample containing IgE antibody binding to the allergen at known concentrations adjusted in a phased manner from 0 (no allergen in the sample) to a concentration sufficient for the allergen to bind to all of the IgE antibodies to perform reaction for a certain time (pretreatment reaction). In the pretreatment reaction, allergen-specific IgE with higher affinity shows preferential binding to the allergen added in a solution, resulting in higher binding ratio to the allergen, and allergen-specific IgE with lower affinity shows lower binding ratio to the allergen.

For the above concentrations adjusted in a phased manner in the pretreatment reaction, concentrations will be suitably determined by those skilled in the art based on, for example, the amount of antibody present in a sample. In the case of allergen dilution in blood plasma, examples of concentrations of diluted allergen include 0 nM, 0.1 nM, 1.0 nM, 10 nM, 100 nM and 1,000 nM (at final concentrations). The concentration of allergen used in the competitive inhibition analysis varies depending on individual allergens. The above certain time for the pretreatment reaction is, for example, 15 minutes to 2 hours, and preferably 30 minutes to 1 hour.

The solution after the above pretreatment reaction is given to a carrier having an extremely high binding sensitivity, such as a DCP chip on which an allergen has been highly immobilized to carry out reaction, for example, by a known method in which the above free antibody is bound to the immobilized allergen; and reaction with a labeled secondary antibody is further carried out, and then the amount of label is measured. In the case of IgE antibody with lower affinity to allergen, the larger amount of the free primary IgE antibody is present in the solution after the above pretreatment reaction and the larger amount of the IgE antibody binds to the immobilized allergen. On the other hand, in the case of IgE antibody with higher affinity to allergen, the smaller amount of the free primary IgE antibody is remaining in the solution after the above pretreatment reaction and the smaller amount of IgE antibody binds to the immobilized allergen.

As described above, the affinity of the respective antibodies to an antigen (allergen) is obtained in terms of the amount of binding of labeled secondary antibody, and the affinity is determined to be high when the amount detected is small, and determined to be low when the amount detected is large. For the quantification of the affinity of IgE antibody to an allergen, when the amount of binding of the labeled secondary antibody detected in a solution which contains no competitive allergen, i.e., in which the concentration of the allergen is 0, is taken as 100%, the concentration of the antigen (e.g., nM in the above example) at which the amount of binding is 50% may be defined as an $IC_{50}$ value.

Examples of the above labeled secondary antibodies include fluorescence dye-labeled secondary antibodies such as HiLyte Fluor 555, Atto532, Cy3, Alexa Fluor 555, Cy5, FITC and rhodamine-labeled secondary antibodies, enzyme-labeled secondary antibodies such as peroxidase and alkaline phosphatase-labeled secondary antibodies, magnetic bead-labeled secondary antibodies and infrared-labeled secondary antibodies.

A chip with a carbon layer formed on the surface of a carrier is preferable as the above chip because it has the advantage of low nonspecific adsorption. A chip into which a chemically modifying group has been introduced and a chip which has been subjected to activation are preferable because they have the advantage in immobilizing peptide. Of them, DCP chips are preferable.

Examples of the above carriers include metals such as gold, silver, copper, aluminum, tungsten, molybdenum, chromium, platinum, titanium and nickel, alloys such as stainless steel and duralumin, laminates of the above metal and ceramics, glass, silicon, fiber, wood, paper, polycarbonate, plastic, and mixed materials of plastic and for example, the above metal and ceramics.

Examples of carbon layers formed on the surface of the carrier include a layer composed of diamond, diamond-like carbon (DLC), amorphous carbon, graphite, hafnium carbide, niobium carbon, silicon carbide, tantalum carbide, thorium carbide, titanium carbide, uranium carbide, tungsten carbide, zirconium carbide, molybdenum carbide, chromium carbide and vanadium carbide.

Examples of chemically modifying groups introduced into the surface of the carrier or into the carbon layer formed on the surface of the carrier include amino group, carboxyl group, epoxy group, formyl group and hydroxyl group.

Examples of methods of introducing the above amino group include a method in which the surface of the carrier or the carbon layer of the chip is irradiated with ultraviolet light in ammonia gas, a method in which the surface of the carrier or the carbon layer of the chip is chlorinated by irradiating with ultraviolet light in chlorine gas and the chlorinated surface of the carrier or carbon layer of the chip is irradiated with ultraviolet light in ammonia gas, and a method in which a polyamine such as methylene diamine and ethylene diamine is reacted with the chlorinated surface of the carrier or carbon layer of the chip.

Examples of methods of introducing the above carboxyl group include a method in which a dicarboxylic acid such as oxalic acid, malonic acid, succinic acid, maleic acid, fumaric acid and phthalic acid or a polycarboxylic acid such as polyacrylic acid, polymethacrylic acid, trimellitic acid and butanetetracarboxylic acid is reacted with the aminated surface of the carrier or carbon layer of the chip.

Examples of methods of introducing the above epoxy group include a method in which an appropriate polyepoxy compound is reacted with the surface of the carrier or carbon layer of the chip aminated as described above and a method in which the carbon=carbon double bond in the carbon layer is reacted with an organic peracid. Examples of organic peracid include peracetic acid, perbenzoic acid, diperoxyphthalic acid, performic acid and trifluoroperacetic acid.

Examples of methods of introducing the above formyl group include a method in which glutaraldehyde is reacted with the aminated surface of the carrier or carbon layer of the chip.

An allergen peptide may also be immobilized on the chip into which the above chemical modifying group has been introduced after an activation treatment by an activating reagent. Examples of methods of immobilizing allergen peptide include a method in which allergen peptide containing amino group (—$NH_2$ group) is immobilized through a covalent bond with carboxyl group (—COOH group) which has been introduced into the surface of a substrate using 1-Etyl-3-(3-dimethylamino propyl)-carbodiimide hydrochloride (WSCD•HCl: Water-Soluble Carbodiimide Hydrochloride), N-Hydroxy-succinimide (NHS) or other chemical crosslinking agent.

Examples of DCP chips described above include a chip prepared by forming, on the surface of a silicon substrate with a DLC treated carbon layer or on the surface of a glass slide, an electrostatic layer which has been treated with an amino-group containing compound or a polymer and/or a copolymer thereof, further superimposing dicarboxylic acid, polycarboxylic acid and the like thereon, and then activating using N-hydroxysuccinimide and/or carbodiimide; a chip obtained by introducing a chemically modifying group into the surface of a carrier or the carbon layer; and a chip which has been subjected to an activation treatment.

When immobilizing the above allergen peptide on a chip, at least one selected from PEG (polyethylene glycol), DMSO (dimethyl sulfoxide), glycine, PBS (phosphate buffered saline), a solution of glycerol, glucose, fructose, mannose, galactose, xylose, inositol, sorbitol, trehalose or cyclodextrin is mixed as an additive for spotting, and the mixture is spotted so as to maintain the function of protein/peptide and/or to increase the amount of binding of protein/peptide to the substrate. These additives for spotting may also be dissolved in a buffer such as CAPS (N-cyclohexyl-3-aminopropanesulfonic acid) buffer and phosphate buffer to be used.

After immobilizing peptide on the chip, blocking treatment is preferably carried out. The blocking treatment can reduce background and can relatively increase fluorescence intensity and color intensity simultaneously, and thus can improve measurement sensitivity. A blocking agent containing no biological components is preferably used as the above blocking agent. When an agent containing no biological components is used, cross-reaction with an animal allergen can be reduced and background noise and reduction in signals can be prevented compared to cases of using a blocking agent containing a biological component such as bovine serum albumin. Specific examples thereof include protein-free blocking buffers such as Pierce Protein-Free Blocking Buffer (available from Thermo Fisher Scientific), Blφk Noise Cancelling Reagent (available from Merck Millipore), Pro-Block (available from ScyTec) and Blockmaster (available from JSR). It is preferable that the blocking agent is added without diluting, then blocking reaction is carried out overnight, and then the blocking agent is washed away and water is removed.

Methods of quantitatively measuring antibody titers using a chip in the present invention are not particularly limited as long as the method is a known immunoassay capable of quantitatively measuring antibody titers by detecting at least IgG1 antibody and IgE antibody, and if necessary IgG2 antibody, to an allergen in a sample. Preferred examples thereof include an ELISA method performed on the chip using a labeled secondary antibody.

Examples of labeled secondary antibodies include fluorescence-labeled secondary antibodies such as HiLyte Fluor 555, Atto532, Cy3, Alexa Fluor 555, Cy5, FITC and rhodamine-labeled secondary antibodies, enzyme-labeled secondary antibodies such as peroxidase and alkaline phosphatase, magnetic bead-labeled secondary antibodies, infrared-labeled secondary antibodies, labeled anti-human IgE antibody, labeled anti-human IgG antibody, labeled anti-human IgA antibody, labeled anti-human IgM antibody and labeled anti-allergen antibody. Fab fragments and F(ab')$_2$ fragments of an antibody may also be used as the above secondary antibody. Fab fragments can be prepared by treating an antibody with papain and the like and F(ab')$_2$ fragments can be prepared by treating with pepsin and the like.

Known chips and methods may be used as the chip on which an allergen is immobilized and as the method of quantitatively measuring IgG1, IgE, and if necessary IgG2 antibodies. Specific examples thereof include the chip and the method disclosed in Japanese Unexamined Patent Application Publication No. 2006-267058, Japanese Unexamined Patent Application Publication No. 2006-267063 and Japanese Unexamined Patent Application Publication No. 2015-169616.

Hereinafter, the present invention will be described in detail with reference to Examples, but the technical scope of the present invention is not limited to the illustration.

EXAMPLES

Example 1

(Samples)

Clinical samples approved by the ethics committee of the Tokushima University and the ethics committee of the Naruto Health Insurance Hospital (Tokushima Prefecture) (Approval No: #1314) with thorough informed consent were provided from the Naruto Health Insurance Hospital: cord blood samples of 84 infants; blood (blood plasma samples) collected at 2 months old, 4 months old, and 6 months old; and blood of the mother of the respective infants (mother's blood plasma samples) were used as samples. Details of 84 infants and their mothers are shown in the following Table 1.

TABLE 1

| Subject | | 84 mother-infant pairs |
|---|---|---|
| Sex | | 42 Male infants (50%) |
| | | 42 Female infants (50%) |
| Feeding type | Breast milk feeding | 31 infants (37%) |
| | Mixed feeding | 47 infants (56%) |
| | Formula milk feeding | 6 infants (7%) |
| Presence of eczema up to 6 months old | Eczema | 42 infants (50%) |
| | No skin eczema | 42 infants (50%) |
| Allergen elimination at 1 year old | Egg elimination (based on the response when ingested in oral tolerance test or the response at home) | 5 infants (6%) |
| | Milk elimination | 0 infants (0%) |

The above 84 infants have been fed with any one of breast milk (probably containing egg allergen from the mother), formula milk (probably containing milk allergen from bovine milk) and both (probably containing both egg and milk allergens). None of them have eaten solid food until 6 months old. Eczema was found in half of the infants at 6-month checkup.

[Measurement Procedure]
(Preparation of Chip)

Egg white (EW)(prepared by Tokushima University), OVA (available from SIGMA) and β-lactoglobulin (BLG available from SIGMA), which are antigen proteins, were used as allergen.

A substrate prepared by forming an amino-group containing electrostatic layer on the surface of silica glass and introducing thereinto negatively charged carboxylic group derived from polyacrylic acid was subjected to a reactivation treatment in a chemical crosslinking agent (100 mM WSC•HCl, 100 mM NHS, 0.1 M potassium phosphate buffer (pH 6.0)) in dark at room temperature for 30 minutes with shaking. The chemical crosslinking agent was discarded after the reaction and then the substrate was washed with MilliQ water with shaking for 1 minutes twice, and water was immediately removed by using a tabletop centrifuge (Allegra™ X-22R Centrifuger, made by Beckman Coulter) to give an activated chip.

(Coupling Reaction of Allergen)

EW (prepared by Tokushima University), OVA (available from SIGMA) and BLG were each dissolved in a solution to which 5 to 30% DMSO or 5 to 30% PEG300 had been added as antigen protein at a concentration of 0.25 to 1.0 mg/mL to give antigen protein solutions. The respective antigen protein solutions prepared were aliquoted into a 384-well flat bottom plate (made by Corning) and 4 nL thereof was spotted on the above activated chip by a microarrayer (OmniGrid Accent made by DIGILAB) and then drying was carried out at 15° C. to 30° C. for 1 to 18 hours to immobilize the antigen protein. A schematic view of the DCP chip on which protein has been immobilized is shown in FIG. 1.

(Blocking Reaction for Unreacted Active Group)

A blocking reagent, Blockmaster (available from JSR), was added to the chip on which the antigen protein was immobilized in a reaction plate (wells), and the chip was left to stand in dark and refrigeration (4° C.) to carry out reaction overnight.

(Capturing Reaction with Allergen Specific Antibody)

After removing the above blocking reagent by suction using an aspirator (VARIABLE SPEED PUMP made by BIORAD), the chip was transferred to the reaction plate again and 8 mL of washing liquid (50 mM TTBS) was added thereto, and after shaking for 5 minutes, the washing liquid was removed by suction by the aspirator. The plate was washed 3 times in the same manner and then further washed with purified water (MilliQ water) 3 times. Water droplets on the surface of the chip were removed by centrifugation (at 2,000 rpm for 1 minutes) using a centrifuge (Allegra (trademark), X-22R Centrifuge (made by BECKMAN COULTER)). A diluted primary antibody solution was prepared by suitably diluting with a sample diluent (20 mM phosphate buffer, pH 7.4/0.3 M KCl/0.05% Tween 20). 10 µL of the diluted primary antibody solution was added to reaction wells and left to stand in dark at 37° C. for 2 hours.

(Reaction with Secondary Antibody)

The diluted sample solution (primary antibody) prepared by the above procedure was removed by suction using an aspirator (VARIABLE SPEED PUMP made by BIORAD) and then the chip was transferred to a case for washing and 10 µL of washing liquid (50 mM TTBS) was added thereto. Then 5-minute washing was repeated 3 times using Double-Shaker NR3. Subsequently, purified water (MilliQ water) was added thereto to carry out 1-minute washing 3 times. Water droplets on the surface of the chip were removed by centrifugation (at 2,000 rpm for 1 minutes) using the above centrifuge. Then, fluorescence-labeled secondary antibodies were prepared in the form of secondary antibody solutions (HiLyte Fluor (trademark) or 555 conjugated anti-human IgE (available from HyTest) (IMMUNO SHOT Platimun/1% bovine serum albumin was used as a diluent, final diluted concentration 10 µg/mL), HiLyte Fluor (trademark) or 555 conjugated anti-human IgG1 (available from Thermo Fisher Scientific) (20 mM phosphate buffer, pH 7.4/1% bovine serum albumin/0.3 M KCl/0.05% Tween 20 was used as a diluent, final diluted concentration 1.5 µg/mL), HiLyte Fluor (registered trademark) or 555 conjugated anti-human IgG2 (available from BIORAD Laboratories (20 mM phosphate buffer, pH 7.4/1% bovine serum albumin/0.3 M KCl/0.05% Tween 20 was used as a diluent, final diluted concentration 1.5 µg/mL). The secondary antibody solution was aliquoted into reaction wells on the slide in 10 µL portions and left to stand in dark at 37° C. for 2 hours.

[Detection of Antibody Captured by Antigen]

The above diluted primary antibody solution was removed by suction using an aspirator and then the chip was put in a case for washing and 5-minute washing was repeated 3 times using Double-Shaker NR3 (made by TAITEC CORPORATION). Subsequently, purified water (MilliQ water) was added thereto to carry out 1-minute washing 3 times and the chip was dried by removing water droplets by centrifugation using the above centrifuge. The fluorescence intensity was measured (Ex: 532 nm, Em: 570 nm) by a fluorescent scanner (3D Gene Scanner made by Toray Industries, Inc.) and the fluorescence intensity of the spots obtained from the respective chips was quantified. For the unit of measurement, the antibody titer of an antibody that bound to an allergen by antigen-antibody reaction was expressed in Binding Unit (BU). The fluorescence intensity was calculated from a calibration curve of the fluorescence intensity of standard antibodies immobilized on a chip at known concentrations. IgE standard antibody, IgG standard antibody, IgG2 standard antibody, IgG3 standard antibody, IgG4 standard antibody and IgA standard antibody were used as standard antibody. In the following, IgE is represented in BUe with 1 BUe=2.3 ng, IgG1 is represented in BUg1 with 1 BUg1=1.0 µg, IgG2 is represented in BUg2 with 1 BUg2=1.0 µg, IgG3 is represented in BUg3 with 1 BUg3=1.0 µg, IgG4 is represented in BUg4 with 1 BUg4=1.0 µg and IgA is represented in BUa with 1 BUa=1.0 µg.

Test Example 1

The antibody titer of IgE antibody, IgG1 antibody and IgG2 antibody against EW in a cord blood sample; and samples collected from 84 infants aged 2 months, 4 months and 6 months was measured. The results are shown in FIGS. 2(a) to (c).

(Results)

As is evident from FIG. 2(a), for the antibody titer of IgE against EW, a small amount of low affinity IgE which was produced by fetus at the embryonic stage against EW allergen transferred from the mother through the placenta was detected in the cord blood. Although the data does not indicate the distinction as to whether the infants were breast-fed or not, the IgE antibody titer rapidly increased in breast-fed infants after 4 months old. The cause may be that an undecomposed component of egg eaten by the mother entered into the body of the infant through breast milk and an antibody reaction against egg white allergen occurred to increase the IgE antibody titer. This can be considered as a usual process of oral immune tolerance that many infants experience. In contrast, the IgE antibody titer did not increase much in some infants; this may be because, since the amount of antigen in breast milk is small or the development of the immune system of the infants is slow, accumulation of antigen specific IgG1 is insufficient before 6 months old and thus the class switching from IgG1 to IgE is delayed.

As is evident from FIGS. 2(b) and (c), the antibody titer of IgG1 and IgG2 against EW is significantly high in cord blood but is rapidly decreased. FIGS. 2(b) and (c) show that a large amount of maternally derived IgG1 and IgG2 transferred from the mother through the placenta in infancy is detected in infants shortly after birth and IgG1 and IgG2 against EW produced in the infants begin to be detected after 2 to 4 months old when the maternally derived IgG disappears. Furthermore, as is evident from FIG. 2(a), IgE against egg white (EW) has been detected in cord blood although IgE is not maternally transferred. This result is consistent with what the present inventors have already found: infants have been sensitized to antigen with an IgG—antigen complex transferred to the infants through the placenta in infancy and as a result low affinity IgE produced in the infants themselves has been detected (Kamemura N, et al. Low-affinity allergen-specific IgE in cord blood and affinity maturation after birth. J Allergy Clin Immunol 2014; 133: 904-905). Since a group showing a pattern of immune tolerance and a group showing no pattern of immune tolerance are considered to have coexisted, studies were continued.

Test Example 2

The antibody titer of IgE antibody, IgG1 antibody and IgG2 antibody against BLG in a cord blood sample; and samples collected from 84 infants aged 2 months, 4 months and 6 months was measured. The results are shown in FIGS. 3(a) to (c).

As is evident from FIG. 3(a), the antibody titer of IgE against BLG is small and low allergen sensitization is found before 2 months old. BLG, which is contained in bovine milk in small amounts and not inherently contained in human breast milk, has relatively high antigenicity, and thus manufactural processing of eliminating BLG is carried out in the preparation of formula milk. However, its complete elimination is difficult with current techniques and about 0.5% to 1.3% of BLG remains in baby formula, and thus ingestion of formula milk leads to sensitization to BLG. In BLG antigen sensitization, a chevron-shaped "immune tolerance pattern" in which the level of antibody is increased shortly after birth and is decreased thereafter was found to have been established in the majority of infants. Since all 84 infants acquired immune tolerance to milk at 1 year old, even those with an increase in the level of antibody up to 6 months old without the above chevron-shaped "immune tolerance pattern" are considered to have followed by the same "immune tolerance pattern" thereafter before 1 year old.

For the occurrence of BLG antibodies up to 6 months old, there are class switching proceeding (IgM) →IgG3→IgG1→IgG2→IgG4 and class switching proceeding IgG3→IgG1→IgE in the order of immunoglobulin gene locus. It has been found that these immunoglobulins appear at different times and while IgG1 and IgE increase and then decrease, IgG2 tends to continue to increase with some exceptions. It has been found that for time-dependent change, IgG1 appeared early and peaked at 2 or 4 months old in many cases, while increase of IgG2 and IgE begins after increase of IgG1. None of the 84 infants in this survey were diagnosed as milk allergy in the antigen challenge test after 1 year and all of them were found to have acquired oral immune tolerance. Thus, FIGS. 3(a) to (c) are considered to show a pattern of fluctuation of IgE, IgG1, IgG2 in the case where oral immune tolerance is acquired.

Example 2

[Correlation Between IgE Antibody Titer and IgG1 Antibody Titer Against BLG]

IgG1 antibody titers and IgE antibody titers against BLG in blood plasma collected from the above 84 infants aged 2 months, 4 months and 6 months were measured, and a scattergram was created by plotting the IgG1 antibody titer on an X axis and the IgE antibody titer on a Y axis. The results are shown in FIGS. 4(a) (2 months old), (b) (4 months old) and (c) (6 months old).

(Results)

Referring to FIGS. 4(a) and (b), regression analysis was performed to analyze relationship between the IgG1 antibody titer and the IgE antibody titer against BLG at 2 months old and 4 months old. In both cases IgG1→IgE class switching occurred at the point where IgG1 exceeded 2,000 BUg1/mL.

Referring to FIG. 4(c), regression analysis was performed to analyze relationship between the IgG1 antibody titer and the IgE antibody titer against BLG at 6 months old. A linear function (Y=0.1677X−335.4) that rises at IgG1 of 2,000 BUg1 was obtained as in the case of 2 months old and 4 months old. In all of FIGS. 4(a) to (c), accumulation of IgG1 was observed with time when infants were subjected to allergen sensitization, and in most cases transfer to IgE did not occur until IgG1 exceeded 2,000 Bug1/mL. We have confirmed that since no infant developed milk allergy, in the case of BLG, data is present within the region to which the above linear function can be applied, for the pattern in which oral immune tolerance has been acquired and the risk of developing allergy can be predicted to be low, and the threshold at which transfer from IgG1 to IgE occurred is 2,000 Bug1. The threshold for class switching of IgG1→IgE and the linear function vary depending on the type of antigens, but for all antigens, class switching is assumed to proceed in a similar pattern.

Example 3

[Correlation Between IgE Antibody Titer and IgG1 Antibody Titer Against EW]

IgG1 antibody titers and IgE antibody titers against EW in blood plasma collected from the above 84 infants aged 2 months, 4 months and 6 months were measured, and a scattergram was created by plotting the IgG1 antibody titer on the X axis and the IgE antibody titer on the Y axis. The results are shown in FIGS. 5(a) (2 months old), (b) (4 months old) and (c) (6 months old).

(Results)

As is evident from FIG. 5(a), the IgG1 antibody titer remains low, with little accumulation of IgG1 at 2 months old. Furthermore, the antibody titer of 2-month old infants in which maternally transferred IgG1 is present is not considered to be reliable in evaluation of the levels of IgG1 produced by the infants. As is evident from FIG. 5(b), accumulation of IgG1 against EW was observed at 4 months old. The graph of 4-month old infants suggests the presence of the threshold for class switching from IgG1 to IgE similar to that in the case of BLG for most of the infants although there are some exceptions.

Referring now to FIG. 5(c), for a linear function applicable to the data distributed over the entire scattergram, the data was divided into two blocks in consideration of the actual distribution of the data, and a linear function applicable to the respective groups was calculated by a software, GraphPad Prism ver. 6.07. As a result, for the correlation between the IgG1 antibody titer and the IgE antibody titer against EW, linear function <1> (Y=0.1274X−178.36, wherein X≥1,400) that rises at IgG1=1,400 BUg1 and linear function <2> (Y=2.131X−852.94, wherein X<1,400, Y≥300) that rises at a value smaller than IgG1=1,400 BUg1 were obtained. Since 90.9% of the infants who belonged to the block to which linear function [2] was applicable had a past history of eczema which had lasted for more than one week up to 6 months old, and since 4 out of 5 infants who had egg allergy at 1 year old belonged to this block, the group was considered to be with a high risk of food allergy. An exceptional infant, who did not belong to the above blocks and developed egg allergy, did not fall under the category of linear function <1> or <2> and showed high IgE and high IgG1; as described later, the IgG1→IgG2 class switching was relatively insufficient and IgG2 remained low, being only slightly above 200 BUg2/mL.

Example 4

[Presence of Eczema in 6 Month Checkup and Steroid Therapy]
(EW)
Information on the presence of eczema in 6 month checkup and whether or not steroid has been applied to a site with eczema was added to FIG. 5(c) and presented in FIG. 6. Infants with eczema (eczema group) are represented by ▲ (triangle), infants without eczema (no eczema group) are represented by ○ (circle), those with eczema who have received steroid therapy are represented by (■) and those who developed egg white allergy at 1 year old are represented by ◇. In most cases steroid intervention was carried out in 4 to 6 months old.

As is evident from FIG. 6, eczema developed with high probability (about 90.9%) in the block to which the above linear function <2> is applicable. Steroid was applied to the site of eczema for 19 infants with a severe symptom of eczema once or twice a day according to the "Guidelines for the Treatment of Atopic Dermatitis." Most of the infants whose IgE antibody titer rapidly increased even with a low IgG1 value suffered from eczema. This may be because EW antigen contained in breast milk came in contact with the skin with impaired barrier function due to eczema, causing percutaneous sensitization. This increase in the levels of IgE was considered to be a consequence of IgG1→IgE class switching caused by a mechanism of percutaneous sensitization different from IgG1→IgE class switching caused by oral sensitization. More specifically, IgG1→IgE class switching probably occurred due to a mechanism of percutaneous sensitization and the IgE antibody titer rapidly increased before IgG1 reached to the threshold levels at which immune tolerance develops.

(BLG)
The BLG specific IgE antibody titer was low in some infants at 6-month checkup, although they had eczema symptoms, and thus they were predicted to have a very low risk of developing an allergy to BLG. For BLG, one of the reasons of low incidence rates of an allergy may be that more than half of the infants already reached to the threshold of IgG1 at which immune tolerance develops at 2 months old. In other words, this suggests that when class switching proceeds and IgG1 exceeds the threshold levels, the situation to which the above linear function <2> applies is unlikely, even if eczema develops and there is a risk of percutaneous sensitization.

[Guidelines of Steroid Therapy and Development of Allergy]
For the above 84 infants, a food intake test for egg and milk was carried out at 1 year old to diagnose development of an allergy, and 5 EW allergy infants were diagnosed as shown in FIG. 6. No infant were diagnosed with milk allergy. 50% of the infants (42 infants) were affected by eczema and steroid hormone was applied to 19 of them; cases in which steroid hormone was applied were substantially evenly distributed in both of linear function <1>, <2> groups. Since oral immune tolerance has been predicted to be established in the linear function <1> group, the group has a low risk of developing EW allergy regardless of the application of a steroid hormone drug. Thus, once infants were determined to belong to the linear function group <1> by the present assessment method, symptomatic therapy with a weak steroid hormone drug is recommended for the transdermal administration of the steroid hormone drug. In contrast, since percutaneous sensitization is thought to have already occurred and have a risk of development of EW allergy in the linear function <2> group, it has been thought that the transdermal administration of steroid performed was insufficient and a stronger steroid hormone drug which exceeded the limit of symptomatic therapy was appropriate. As described above, an appropriately potent steroid hormone drug can be probably selected at an appropriate time to avoid percutaneous sensitization by using the present "method for collecting data to predict an infant's risk of developing an allergy."

Example 5

[Correlation Between IgG2 Antibody Titer and IgG1 Antibody Titer Against BLG, EW]
FIG. 7 is a graph showing IgG1→IgG2 class switching against BLG (a), EW (b) of 84 infants aged 6 months. When oral immune tolerance is induced, IgG1→IgG2 class switching occurs in addition to IgG1→IgE class switching almost simultaneously. Since production of IgG2 shifts to production of IgG4 due to class switching, this seems to be important for establishment of oral immune tolerance (James L K, et al. Long-term tolerance after allergen immunotherapy is accompanied by selective persistence of blocking antibodies. J Allergy Clin Immunol 2011; 127:509-516; Sugimoto M, et al. Differential response in allergen-specific IgE, IgGs, and IgA levels for predicting outcome of oral immunotherapy. Pediatr Allergy Immunol 2016; 27(3):276-282).

FIG. 7(a) shows IgG1→IgG2 class switching against BLG. A scattergram was created by plotting the IgG1 antibody titer on the X axis and the IgE antibody titer on the Y axis to obtain a linear function of (Y=0.2289X−457.8, wherein X≥2,000). In this case, the threshold for IgG1 was 2,000 BUg1, which was the same as the threshold for IgG1→IgE class switching. This suggests that in the case of BLG where oral immune tolerance has been established, IgG1→IgE class switching and IgG1→IgG2 class switching proceed almost simultaneously when the threshold for IgG1 is reached. FIG. 7(b) shows IgG1→IgG2 class switching against EW. A scattergram was created by plotting the IgG1 antibody titer on the X axis and the IgG2 antibody titer on the Y axis to obtain a linear function of (Y=0.0293X+41.0). The threshold for IgG1→IgG2 class switching, which was considered to be the same as the threshold for IgG1→IgE class switching, was estimated to be 1,400 BUg1. The IgG2 value of all 5 infants who developed EW allergy was 200 BUg2 or less, suggesting that low production of IgG2 is associated with the development of EW allergy.

Example 6

[Correlation Between IgE Antibody Titer and IgG2 Antibody Titer Against EW]
Considering that 5 out of 84 infants developed EW allergy, for the correlation between IgG2 and IgE with class switching of IgG1, IgE antibody titers and IgG2 antibody titers against EW were measured to prepare a scattergram.

The results are shown in FIG. 8. 5 infants with EW allergy were represented by ◇, 42 infants with eczema were represented by ▲ and 42 infants without eczema were represented by ○.

As is evident from FIG. 8, in infants with EW allergy, the level of increase of IgG2 was much smaller than the level of increase of IgE. This confirms that when class switching from IgG1 to IgE proceeds and class switching from IgG1 to IgG2 does not proceed, EW allergy occurs with high probability after 1 year old. The cause may be percutaneous sensitization to EW allergen due to eczema considering that 4 of 5 infants with EW allergy are affected by eczema. The other 1 egg allergy infant did not have eczema and did now show any increase in IgE values, IgG1 values or IgG2 values at 6 months old, and thus some EW antigen sensitization seems to have occurred after 6 months old.

Example 7

[Measurement of Affinity of IgE Antibody for Allergen]

OVA, one of the main components of EW, was used as a single allergen having a known molecular weight. The antibody titer of IgG1 antibody and IgE antibody against OVA in a blood plasma sample collected from a total of 78 6-month old infants including 31 breast-fed infants who may be exposed to OVA contained in breast milk and 47 mixed-fed infants out of 84 infants above was measured. The affinity of IgE antibody against OVA was also measured.

(Preparation of Chip)

A DCP chip on which OVA was immobilized as an antigen protein was prepared in the same manner as in (Preparation of chip) and (Coupling reaction of allergen), [Measurement procedure] in Example 1 except for using an antigen protein OVA (available from SIGMA) as an allergen.

(Capturing Reaction with OVA Specific Antibody)

Before use, a blocking reagent (Blockmaster available from JSR) was added to reaction wells and the chip was left to stand in dark and refrigeration (4° C.) overnight. After removing the above blocking reagent by suction using an aspirator (VARIABLE SPEED PUMP made by BIORAD), the chip was transferred to the reaction plate again and 8 mL of washing liquid (50 mM TTBS) was added thereto, and after shaking for 5 minutes, the washing liquid was removed by suction by the aspirator. The plate was washed 3 times in the same manner and then further washed with purified water (MilliQ water) 3 times. Water droplets on the surface of the chip were removed by centrifugation (at 2,000 rpm for 1 minute) using a centrifuge (Allegra (trademark), X-22R Centrifuge (made by BECKMAN COULTER)).

(Primary Antibody Reaction)

Blood plasma of each infant was diluted 2 to 5 times with a sample diluent (20 mM phosphate buffer pH 7.4/0.3 M KCl/0.05% Tween 20) for the measurement of IgE, and 50 times with the above sample diluent for the measurement of IgG1 and IgG2. Then 10 µL each was aliquoted into the well of the DCP chip and left to stand in dark at 37° C. for 1 hour.

(Reaction with Secondary Antibody)

The diluted blood plasma (primary antibody) prepared by the above procedure was removed by suction using an aspirator (VARIABLE SPEED PUMP made by BIORAD) and then the chip was transferred to a case for washing and 10 µL of washing liquid (50 mM TTBS) was added thereto. Then 5-minute washing was repeated 3 times using Double-Shaker NR3. Subsequently, purified water (MilliQ water) was added thereto to carry out 1-minute washing 3 times. Water droplets on the surface of the chip were removed by centrifugation (at 2,000 rpm for 1 minutes) using the above centrifuge. Then, fluorescence-labeled secondary antibodies were prepared (HiLyte Fluor (trademark) or 555 conjugated anti-human IgE (available from HyTest))(IMMUNO SHOT Platimun/1% bovine serum albumin was used as a diluent; final diluted concentration 10 µg/mL), HiLyte Fluor (trademark) or 555 conjugated anti-human IgG1 (available from Thermo Fisher Scientific) (20 mM phosphate buffer, pH 7.4/1% bovine serum albumin/0.3 MKCl/0.05% Tween 20 was used as a diluent; final diluted concentration 1.5 µg/mL), HiLyte Fluor (registered trademark) or 555 conjugated anti-human IgG2 (available from BIORAD Laboratories) (20 mM phosphate buffer, pH 7.4/1% bovine serum albumin/0.3 M KCl/0.05% Tween 20 was used as a diluent; final diluted concentration 1.5 µg/mL). The secondary antibody solution was aliquoted into reaction wells in 10 portions and left to stand in dark at 37° C. for 2 hours.

A scattergram was created by plotting the IgG1 antibody titer against OVA in blood plasma collected from 6-month old infants on the X axis and the IgE antibody titer on the Y axis. The results are shown in FIG. 9.

As is evident from FIG. 9, the data distributed over the entire scattergram was divided into two blocks and a linear function applicable to the respective groups was calculated by a software, GraphPad Prism ver. 6.07. Block 1 is a group with IgG1 of 2,000 BUg1/mL, and Block 2 is a group with IgG1 of 2,000 BUg1/mL or less and IgE of 300 BUe/mL or more.

For the correlation between the IgG1 antibody titer and the IgE antibody titer against OVA, linear function 1 ($Y=0.1086X-160.2$, wherein $X \geq 2,000$) that rises at IgG1=2,000 BUg1 (hereinafter also referred to as linear function <1>) and linear function 2 ($Y=1.372X-47.619$, wherein $X<2000$, $Y \geq 300$) that rises at a value smaller than IgG1=2,000 BUg1 (hereinafter also referred to as linear function <2>) were obtained.

For the above 78 breast-fed infants and mixed-fed infants, 10 infants were randomly selected as Group [1] out of the infants who belonged to linear function <1> in FIG. 9 in the region surrounded by the dashed line where the infants showed an IgG1 value of 2,000 BUg1 or more and an IgE value of 100 BUe/mL or more at which the antigen affinity of IgE antibody could be measured. Furthermore, 10 infants were randomly selected as Group [2] out of the infants who belonged to linear function <2> in the region surrounded by the solid line where the infants showed an IgG1 value of 2,000 BUg1 or less and an IgE antibody value of 500 BUe/mL or more.

The total 20 infants including the 10 infants who belonged to Group [1] and the 10 infants who belonged to Group [2] were investigated for the affinity of IgE for OVA in the respective blood plasma samples. OVA (0, 0.2, 2, 20, 200, 2000 nM) dissolved in a sample diluent (20 mM phosphate buffer pH 7.4/0.3 M KCl/0.05% Tween 20) was added to blood plasma of the respective infants in an equal amount to give a reaction solution in which the final concentration of OVA was adjusted to 0, 0.1, 1, 10, 100, 2000 nM. The reaction solution was reacted at 25° C. for 30 minutes to carry out pretreatment reaction (competitive binding inhibition reaction). The solution was introduced into the above DCP chip and reaction was carried out at 37° C. for 1 hour.

Subsequently, the solution was removed by suction using an aspirator and then the chip was transferred to a case for washing and 10 µL of washing liquid (50 mM TTBS) was added thereto. Then 5-minute washing was repeated 3 times using Double-Shaker NR3. Subsequently, purified water (MilliQ water) was added thereto to carry out 1-minute washing 3 times. Water droplets on the surface of the chip were removed by centrifugation (at 2,000 rpm for 1 minutes) using the above centrifuge. Then, a secondary antibody solution prepared by diluting 555 conjugated anti-human IgE antibody with an antibody diluent (IMMUNO SHOT Platimun/1% bovine serum albumin) at a final diluted concentration of 10 µg/mL was aliquoted into reaction wells on the slide and left to stand in dark at 37° C. for 2 hours to be reacted with anti-human IgE secondary antibody. 10 µL of washing liquid (50 mM TTBS) was added thereto again and then 5-minute washing was repeated 3 times using Double-Shaker NR 3. Subsequently, purified water (MilliQ water) was added thereto to carry out 1-minute washing 3 times. The amount of fluorescence remaining was measured (Ex: 532 nm, Em: 570 nm) by a fluorescent scanner (3D Gene Scanner made by Toray Industries, Inc.) to quantify the fluorescence intensity of the spots obtained from the respective chips. With the fluorescence intensity in the case where no competitive allergen is present, i.e., the concentration of the competitive substance ovalbumin is 0, being taken as 100%, the concentration of antigen at which the fluorescence intensity is 50% is shown in the section of "IgE $IC_{50}$" in Table 2 below. FIG. 10 schematically illustrates $IC_{50}$ values of infants belonging to linear function [1] and infants belonging linear function [2].

TABLE 2

| Infant No. | Feeding of milk | Group | OVA specific antibody | | |
|---|---|---|---|---|---|
| | | | IgE (BUe/mL) | IgE $IC_{50}$ | IgG1 (BUg1/mL) |
| 2 | Mixed-feeding | [1] | 434.94 | 25.36 | 4552.76 |
| 5 | Mixed-feeding | [1] | 243.75 | 57.21 | 3081.56 |
| 9 | Mixed-feeding | [1] | 108.74 | 90.33 | 4439.77 |
| 10 | Mixed-feeding | [2] | 771.02 | 9.24 | 1287.60 |
| 12 | Mixed-feeding | [1] | 169.68 | 6.97 | 2417.21 |
| 13 | Mixed-feeding | [1] | 720.1 | 75.29 | 5975.70 |
| 24 | Mixed-feeding | [1] | 159.09 | 7.77 | 1680.21 |
| 34 | Mixed-feeding | [2] | 1258.83 | 6.53 | 1002.23 |
| 45 | Mixed-feeding | [1] | 221.61 | 61.26 | 2415.57 |
| 47 | Mixed-feeding | [2] | 825.15 | 1.85 | 790.77 |
| 49 | Breast-feeding | [1] | 446.78 | 8.69 | 3189.44 |
| 64 | Breast-feeding | [1] | 452.37 | 78.03 | 6142.96 |
| 71 | Breast-feeding | [2] | 1176.20 | 8.28 | 737.87 |
| 73 | Mixed-feeding | [1] | 469.79 | 47.33 | 2145.00 |
| 74 | Mixed-feeding | [2] | 916.93 | 15.41 | 593.76 |
| 76 | Mixed-feeding | [2] | 928.63 | 4.64 | 522.47 |
| 80 | Breast-feeding | [2] | 1567.23 | 6.68 | 410.28 |
| 81 | Breast-feeding | [2] | 503.95 | 5.29 | 480.41 |
| 82 | Breast-feeding | [2] | 903.92 | 6.31 | 434.81 |
| 83 | Breast-feeding | [2] | 1517.27 | 18.81 | 168.12 |

(Results)

The median $IC_{50}$ value was 52.27 nm and the mean $IC_{50}$ value was 45.82 nM in Group [1]. The median $IC_{50}$ value was 6.605 nM and the mean $IC_{50}$ value was 8.30 nM in Group [2]. As is evident from FIG. 10, a significant difference (P=0.001) (according to Mann-Whitney U test) in $IC_{50}$ (nM) values was found between Group [1] and Group [2]. The results show that the affinity of IgE for an antigen is low in infants who belong to linear function [1] and has a low risk of developing an allergy to an allergen, while the affinity of IgE for an antigen is high in infants who belong to linear function [2] applied to data of infants with a high risk of developing an allergy to an allergen. The measurement of $IC_{50}$ values which indicate antigen affinity has been confirmed to be an important and useful indicator for predicting the risk of developing an allergy.

CONCLUSION

The above results have revealed that the affinity of IgE for antigen OVA is low in linear function 1 group and the affinity of IgE for antigen OVA is high in linear function 2 group. Infants with IgE whose affinity for an allergen is low can be assessed to have a low risk of developing an allergy and infants with IgE whose affinity for an allergen is high can be assessed to have a high risk of developing an egg allergy. The measurement of $IC_{50}$ values which indicate affinity has been confirmed to be an important indicator for predicting the risk of developing an allergy.

The invention claimed is:

1. A method for reducing a risk of developing an allergy to an allergen in infancy, of a 6-month old or younger infant, the method comprising the following steps (a) to (e):
    (a) quantitatively measuring each of IgG1 and IgE antibody titers against an allergen in a sample collected from an infant;
    (b) creating a scattergram by plotting the IgG1 antibody titer on an X axis and the IgE antibody titer on a Y axis;
    (c) calculating a correlation between the IgG1 antibody titer and the IgE antibody titer by regression analysis into: (1) linear function 1 represented by Y1=aX1−b, wherein a>0, b>0; and (2) linear function 2 represented by Y2=cX2−d, wherein c>a;
    (d) assigning an infant belonging to linear function 1 as having a low risk of developing an allergy to the allergen and assigning an infant belonging to linear function 2 as having a high risk of developing an allergy to the allergen; and
    (e) performing a transdermal administration of steroid to sites where a rash is present in the infant belonging to the linear function 2, having developed eczema up to 6 months and with a high risk of developing an allergy to the allergen, or allowing the infant belonging to linear function 2, having developed eczema up to 6 months old and with a high risk of developing an allergen to the allergen, to have continuous and safe ingestion of antigen.

2. The method according to claim 1, wherein the IgG1 and IgE antibody titers against the allergen in the sample are quantitatively measured by using a densely carboxylated protein (DCP) chip which is a chip prepared by forming, on a surface of a silicon substrate with a diamond-like carbon-treated carbon layer.

3. The method according to claim 1, wherein the sample is blood plasma or blood serum.

* * * * *